(12) United States Patent
Scott et al.

(10) Patent No.: US 6,929,630 B2
(45) Date of Patent: Aug. 16, 2005

(54) INFUSION CLAMP

(75) Inventors: Bradford G. Scott, Houston, TX (US); Matthew J. Wall, Sugarland, TX (US)

(73) Assignee: Baylor College of Medicine, Houston, TX (US)

( * ) Notice: Subject to any disclaimer, the term of this patent is extended or adjusted under 35 U.S.C. 154(b) by 113 days.

(21) Appl. No.: 10/430,248

(22) Filed: May 6, 2003

(65) Prior Publication Data

US 2003/0212365 A1 Nov. 13, 2003

Related U.S. Application Data

(60) Provisional application No. 60/378,582, filed on May 7, 2002.

(51) Int. Cl.[7] .............................................. A61M 31/00
(52) U.S. Cl. ............... 604/500; 604/174; 128/DIG. 26; 606/151; 606/207; 606/205; 24/455
(58) Field of Search ................................. 604/174, 513, 604/176–180, 539, 523, 500; 128/DIG. 26; 606/151–158, 207, 208, 205; 24/455

(56) References Cited

U.S. PATENT DOCUMENTS

| | | | |
|---|---|---|---|
| 2,387,928 A | | 10/1945 | Monnier |
| 2,468,823 A | | 5/1949 | Houseplan |
| 2,977,150 A | | 3/1961 | Thomas |
| 3,446,211 A | | 5/1969 | Markham |
| 3,980,086 A | * | 9/1976 | Kletschka et al. ............. 604/35 |
| 3,999,555 A | | 12/1976 | Person |
| 4,049,002 A | * | 9/1977 | Kletschka et al. ............. 604/35 |
| 4,484,911 A | * | 11/1984 | Berlin et al. ................. 604/174 |
| 4,608,982 A | | 9/1986 | Pollard |
| 4,611,592 A | | 9/1986 | Talboy |
| 4,792,330 A | * | 12/1988 | Lazarus et al. ............. 604/174 |
| 4,817,604 A | * | 4/1989 | Smith, III ................... 606/151 |
| 5,019,092 A | | 5/1991 | Klintmalm |
| 5,127,915 A | * | 7/1992 | Mattson ...................... 606/120 |
| 5,391,181 A | | 2/1995 | Johnson et al. |
| 5,514,148 A | * | 5/1996 | Smith, III ................... 606/151 |
| 5,772,670 A | | 6/1998 | Brosa |
| 5,931,810 A | * | 8/1999 | Grabek ....................... 604/506 |
| 6,152,920 A | | 11/2000 | Thompson et al. |
| 6,293,920 B1 | | 9/2001 | Sweezer et al. |
| 6,761,725 B1 | * | 7/2004 | Grayzel et al. ............. 606/174 |
| 2001/0016750 A1 | | 8/2001 | Malecki et al. |
| 2001/0031961 A1 | | 10/2001 | Hooven |
| 2001/0041915 A1 | | 11/2001 | Roue et al. |
| 2003/0120306 A1 | * | 6/2003 | Burbank et al. ............ 606/205 |

* cited by examiner

*Primary Examiner*—Cris L. Rodriguez
(74) *Attorney, Agent, or Firm*—Conley Rose, P.C.

(57) ABSTRACT

The present invention is directed to an infusion clamp including a first clamping member having a first side surface, a second side surface, a first mating surface, and an aperture disposed between the first side surface and the second side surface thereby forming a passageway there between; a second clamping member having a third side surface, a fourth side surface, and a second mating surface; a hinge member disposed along and in communication with first clamping member and second clamping member, thereby facilitating the movement of the infusion device from the closed position of the infusion clamp to the plurality of opened positions of the infusion clamp, and from the plurality of opened positions to the closed position; and an infusion device support member disposed above the passageway thereby permitting an infusion device to be disposed within the infusion device support member and through the passageway. The infusion clamp permits quick and easy attachment of an infusion device, e.g., a catheter, to a chambered body, e.g., the right atrium of the heart, for infusion of fluid into the chambered body such as during emergency surgery or triage on a patient. Methods of infusing chambered bodies are also disclosed.

22 Claims, 4 Drawing Sheets

US 6,929,630 B2

INFUSION CLAMP

RELATED APPLICATION

This application claims the benefit of U.S. Provisional patent application Ser. No. 60/378,582, filed May 7, 2002.

BACKGROUND OF THE INVENTION

1. Field of the Invention

The present invention is directed to an infusion clamp, and in particular, an infusion clamp for securing an infusion device, e.g., a catheter, to the wall of a chambered body such as the right atrium of the heart for quick and easy infusion of fluid into the chambered body. The present invention is also directed to a method of infusing a chambered body with a fluid using the infusion clamps of the present invention.

2. Description of Related Art

During medical emergencies, physicians are sometimes required to infuse, or instill, a large amount of fluid into a patient's body, and more specifically, a chambered body such as the heart. In particular, after traumatic accidents in which a patient has lost a large amount of blood, an emergency room physician is required to access the heart through the patient's chest, insert an infusion device, e.g., a catheter, and infuse the heart with blood or other fluid in an attempt to stabilize the patient for further surgery or other actions. In this situation, the fluid is infused into the heart through the right atrium.

One problem with prior techniques and devices for infusing the right atrium with fluid is that the techniques and devices are cumbersome and take time to be put in place. As is apparent, patients requiring fluid infusion into their hearts do not have time on their side. As the amount of time for infusing the heart increases, the probability that the patient will survive the procedure decreases. Accordingly, prior to the development of the present inventions, there has been no infusion clamp or method of infusing a chambered body that: permit quick and easy connection of the infusion device to the chambered body; permit quick and easy insertion of the infusion device into the chambered body; and provide a single apparatus for securing an infusion device to a chambered body. Therefore, the art has sought an infusion clamp and a method of infusing a chambered body that: permit quick and easy connection of the infusion device to the chambered body; permit quick and easy insertion of the infusion device; and provide a single apparatus for securing an infusion device to a chambered body. It is believed that the present inventions will achieve these objectives and overcome the disadvantages of other infusion clamps and a methods of infusing a chambered body but their results or effects are still dependent upon the skill and training of the operators and surgeons.

SUMMARY OF INVENTION

In accordance with the invention the foregoing advantages have been achieved through the present infusion clamp having a plurality of opened positions and a closed position, the infusion clamp comprising: a first clamping member having a first side surface, a second side surface, a first mating surface, and an aperture disposed between the first side surface and the second side surface thereby forming a passageway disposed between the first side surface and the second side surface; a second clamping member having a third side surface, a fourth side surface, and a second mating surface; a hinge member disposed along and in communication with the first clamping member and the second clamping member, thereby facilitating the movement of the infusion device from the closed position to the plurality of opened positions and from the plurality of opened positions to the closed position; and an infusion device support member disposed above the passageway thereby permitting an infusion device to be disposed within the infusion device support member and through passageway.

A further feature of the infusion clamp is that the infusion device support member and the passageway may be disposed at an angle substantially perpendicular to the first side surface and the second side surface. Another feature of the infusion clamp is that the infusion device support member may include a recess having a shape complementary to the infusion device. An additional feature of the infusion clamp is that the shape of the recess may be complementary to a catheter. Still another feature of the infusion clamp is that the infusion clamp may further comprise at least one gripping member. A further feature of the infusion clamp is that the infusion clamp may further comprise at least two gripping members and a locking member. Another feature of the infusion clamp is that each of the at least two gripping members may include a finger loop. An additional feature of the infusion clamp is that the first clamping member and the second clamping member may be curved shaped. Still another feature of the infusion clamp is that the first clamping member and the second clamping member may each include two ends; and the hinge member may be disposed at one of the two ends of each of the first clamping member and the second clamping member.

In accordance with the invention the foregoing advantages have also been achieved through the present infusion clamp having a plurality of opened positions and a closed position, the infusion clamp comprising: a first clamping member having a first side surface, a second side surface, a first mating surface, and a first aperture forming a first partial passageway disposed between the first side surface and the second side surface; a second clamping member having a third side surface, a fourth side surface, a second mating surface, and a second aperture forming a second partial passageway disposed between the third side surface and the fourth side surface, wherein the first partial passageway and the second partial passageway form a complete passageway when the infusion clamp is placed in the closed position; a hinge member disposed along and in communication with the first clamping member and the second clamping member, thereby facilitating the movement of the infusion device from the closed position to the plurality of opened positions and from the plurality of opened positions to the closed position; and an infusion device support member disposed above the first partial passageway thereby permitting an infusion device to be disposed within the infusion device support member and through the first partial passageway when the infusion device is placed in one of the plurality of opened positions, and through the complete passageway when the infusion device is placed in the closed position.

A further feature of the infusion clamp is that the infusion device support member and the complete passageway may be disposed at an angle substantially perpendicular to the first side surface and the second side surface. Another feature of the infusion clamp is that the infusion device support member may include a recess having a shape complementary to the infusion device. An additional feature of the infusion clamp is that the shape of the recess may be complementary to a catheter. Still another feature of the infusion clamp is that the infusion clamp may further comprise at least one gripping member. A further feature of the infusion clamp is that the infusion clamp may further comprise at least two gripping members and a locking member. Another feature of the infusion clamp is that each of the at least two gripping members may include a finger loop. An additional feature of the infusion clamp is that the first clamping member and the second clamping member may be curved shaped. Still another feature of the infusion clamp is that the first clamping member and the second clamping member may each include two ends; and the hinge member may be disposed at one of the two ends of each of the first clamping member and the second clamping member.

In accordance with the invention, the foregoing advantages have also been achieved through the present method of infusing a chambered body having an outer wall and a cavity, the method comprising the steps of: (a) providing an infusion device; (b) providing an infusion clamp having a plurality of opened positions, a closed position, at least two clamping members, a hinge member disposed along and in communication with the at least two clamping members, and an infusion device support member, each of the at least two clamping members including a topside surface, a bottom side surface, a mating surface, and a partial passageway formed between the topside surface and the bottom side surface of the respective clamping members, whereby the partial passageways of each of the clamping members form a complete passageway when the infusion clamp is in the closed position, and the infusion device support member is disposed above the partial passageway of one of the at least two clamping members such that the infusion device is disposed within the infusion device support member and through the partial passageway of one of the at least two clamping members when the infusion clamp is in one of the plurality of opened positions; (c) placing the infusion clamp on the outer wall of the chambered body and moving the infusion clamp from one of the plurality of opened positions to the closed position thereby securing the infusion clamp the outer wall of the chambered body; (d) inserting the infusion device into the infusion device support member and through the complete passageway; (e) inserting the infusion device through the outer wall of the chambered body thereby providing fluid communication with the cavity of the chambered body; and (f) infusing the cavity of the chambered body with at least one fluid through the infusion device.

A further feature of the method of infusing a chambered body is that the infusion device may be connected to a fluid source prior steps (d) and (e). Another feature of the method of infusing a chambered body is that step (d) may occur prior to step (c). An additional feature of the method of infusing a chambered body is that the infusion device may be connected to a fluid source prior step (d).

The infusion clamp and method for infusing a chambered body, have the advantages of: permitting quick and easy connection of the infusion device to the chambered body; permitting quick and easy insertion of the infusion device; and providing a single apparatus for securing an infusion device to a chambered body. As mentioned above, it is believed that the present inventions will achieve these objectives and overcome the disadvantages of other surgical devices and surgical systems and methods in the field of the invention, but their results or effects are still dependent upon the skill and training of the operators and surgeons.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION AND SPECIFIC EMBODIMENTS

Broadly, the present invention is directed to improved infusion clamps and methods of infusing a chambered body with fluid. The infusion clamps provide a seal to the chambered body to permit large volumes of fluid to be transfused into the chambered body. As used herein, "chambered body" is defined as an organ, body cavity, artery, e.g., the aorta, vein, e.g., the vena cava, or other body part that includes at least one outer wall and at least one chamber or cavity which may require the infusion, or instillation, of a large volume of fluid. For example, during resuscitative thoracotomy, large volumes of fluid or blood are require to be infused into the right atrium of the heart. The infusion clamps of the present invention are useful in such a procedure because the infusion clamp can be easily secured to the appendage of the right atrium and a catheter can then be easily secured to the infusion clamp and inserted through the infusion clamp and through the outer wall of the right atrium thereby providing fluid access to the cavity of the right atrium. The infusion clamp is secured to the chambered body by moving the infusion clamp from one of its plurality of opened positions to its closed position, i.e., the position at which the infusion clamp is secured to the chambered body, or, as discussed below, if no chambered body is being clamped, the position that the two mating surfaces of the two clamping members of the infusion device are in contact with each other.

Figure 1:
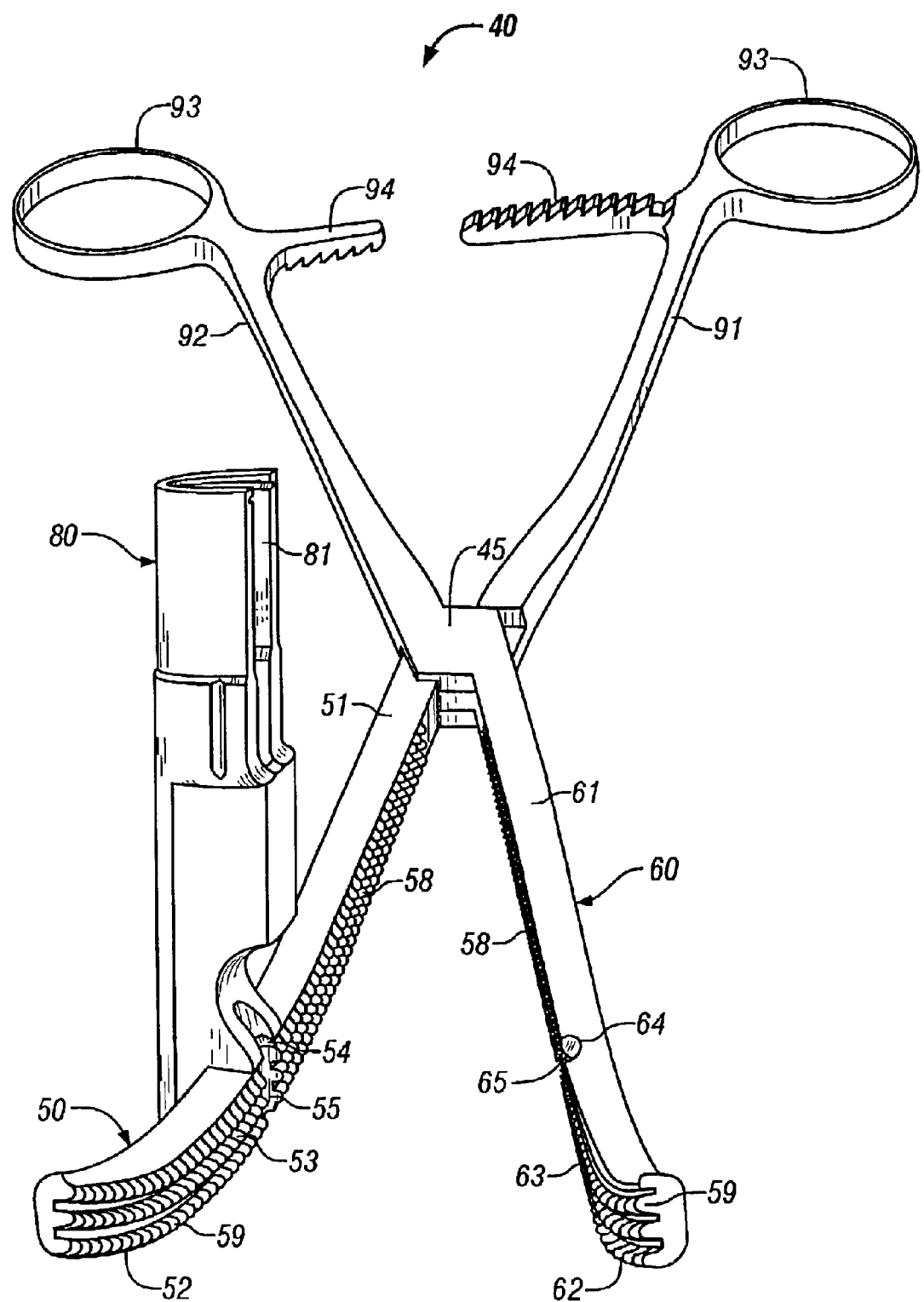
FIG. 1 is a perspective view of one specific embodiment of the infusion clamp of the present invention in one of the plurality of opened positions.
Figure 2:
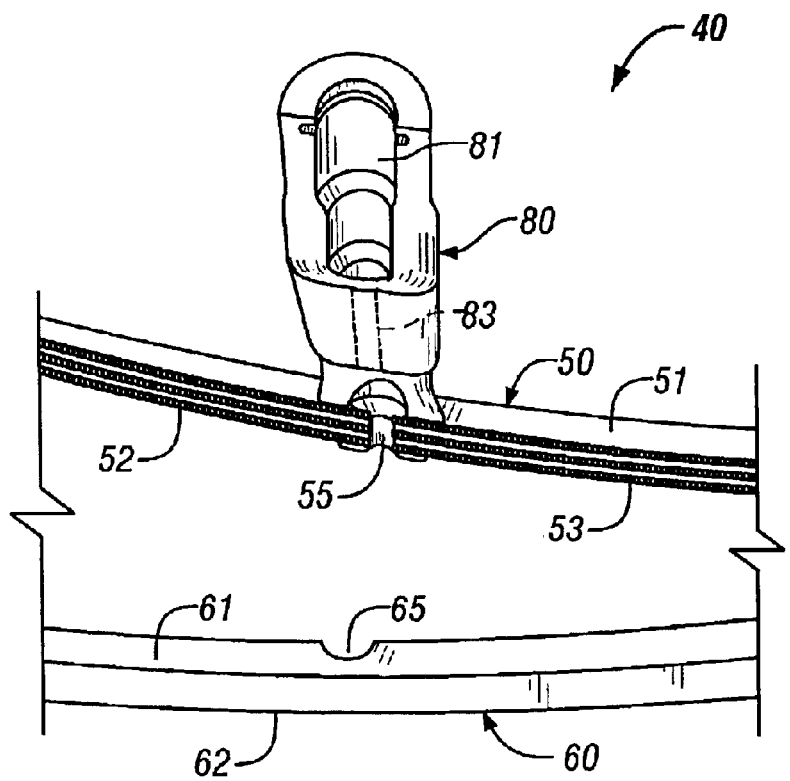
FIG. 2 is a perspective partial view of the infusion clamp shown in FIG. 1 in one of the plurality of opened positions.

Referring now to FIGS. 1–6, broadly, infusion clamp 40 includes first clamping member 50, second clamping member 60, and hinge member 45. In the embodiment shown in FIGS. 1–4, infusion clamp 50 also includes first gripping member 91, second gripping member 92, finger loops 93, and locking member 94 which facilitate an operator of infusion clamp 40 to hold and manipulate infusion clamp 40 to secure infusion clamp 40 to the side of a chambered body (not shown). Thereafter, both hands of the operator are freed to insert the infusion device, e.g., a catheter, into and through infusion clamp 40 and into the chambered body. In the embodiment in which infusion clamp 40 includes at least two gripping members, 91, 92, hinge member 45 is preferably disposed between gripping members 91, 92 and clamping members 50, 60 (FIG. 1).

Alternatively, infusion clamp 40 may not include gripping members 91, 92. In this embodiment, illustrated in FIG. 6, hinge member 45 is preferably disposed at one of the two ends of each of first and second clamping member 60, 70.

First clamping member 50 includes topside surface 51, bottom side surface 52, and first mating surface 53. Aperture 54 is disposed between topside surface 51 and bottom side surface 52 to create partial passageway 55 between topside surface 51 and bottom side surface 52. As illustrated in FIGS. 1–4 and 6, aperture 54 is disposed along topside surface 51 and first mating surface 53.

Likewise, second clamping member 60 includes topside surface 61, bottom side surface 62, and second mating surface 63. In one specific embodiment, shown in FIGS. 1–4, second clamping member 60 also includes aperture 64 disposed between topside surface 61 and bottom side surface 62 to create second partial passageway 65 between topside surface 61 and bottom side surface 62. As illustrated in FIGS. 1–4 and 6, aperture 64 is disposed along topside surface 61 and second mating surface 63.

Preferably, second mating surface 63 is complementary to first mating surface 53 to facilitate clamping infusion clamp 40 to a chambered body. Additionally, first mating surface 53 and second mating surface 63 each preferably include textured surface 58, e.g., protrusions 59, to facilitate securing infusion clamp 40 to the chambered body. Also, first clamping member 50 and second clamping member 60 preferably have a curved shape.

Figure 3:
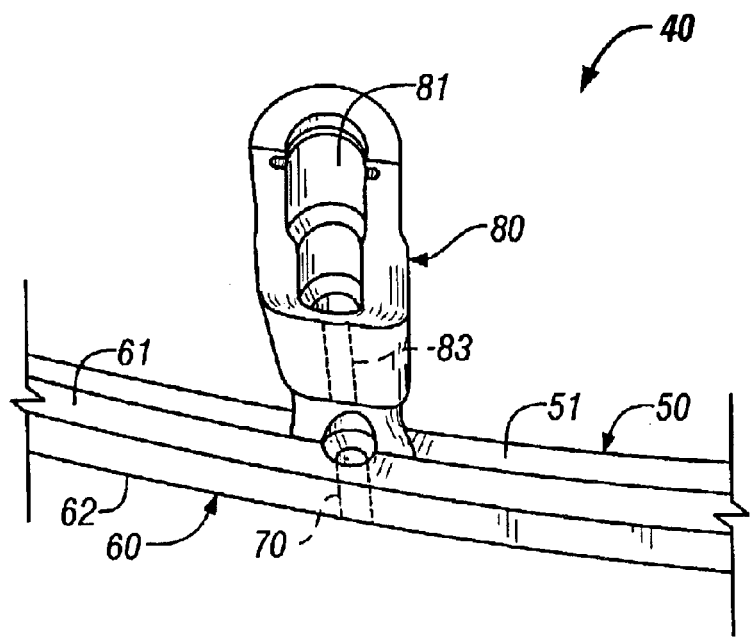
FIG. 3 is a perspective partial view of the infusion clamp shown in FIG. 1 in the closed position.
Figure 4:
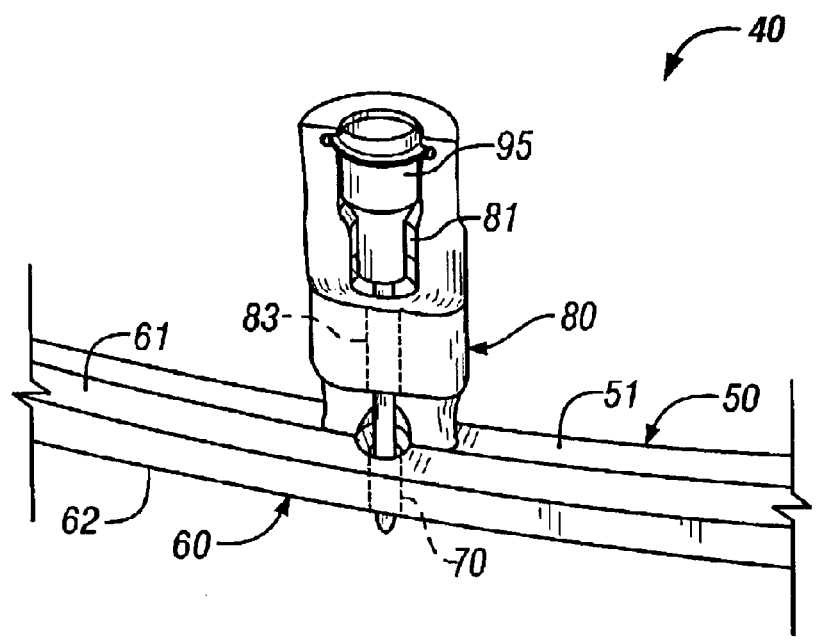
FIG. 4 is a perspective partial view of the infusion clamp shown in FIG. 1 in the closed position and having a catheter disposed within the infusion device support member.

In the specific embodiment shown in FIGS. 1–4, apertures 54, 64 are designed such that when infusion clamp 40 is placed in its closed position, complete passageway 70 is formed by partial passageway 55 and second partial passageway 65. In this embodiment, apertures 54, 64 have a substantially continuous circumference when complete passageway 70 is formed by the movement of infusion clamp 40 to the closed position. "Substantially continuous" is defined herein as a circumference that is formed by the mating of two complementary surfaces, e.g., first mating surface 53 and second mating surface 63, having one portion of the circumference being formed by one mating surface and the other portion of the circumference being formed by a second mating surface e.g., first clamping member 50 and second clamping member 60 contact one another in the closed position (FIGS. 3 and 4). It is to be understood, however, that when infusion clamp 40 is secured to the chambered body, first mating surface 53 and second mating surface 63 may not contact one another due to the portion of the outer wall of the chambered body being clamped between first mating surface 53 and second mating surface 63. Nevertheless, infusion clamp 40 is in the closed position and apertures 54, 64 form a substantially continuous circumference.

In the embodiment shown in FIGS. 1–4, the substantially continuous circumference is circularly-shaped with one-half of the circularly-shaped circumference being formed by aperture 54 and passageway 55 of first clamping member 50 and one-half of the circularly-shaped circumference being formed by aperture 64 and passageway 65 of second clamping member 60. It is to be understood, however, that complete passageway 70 may be formed solely through either first clamping member 50 (FIG. 5) or second clamping member 60.

Disposed along topside surface 51 or topside surface 61 is infusion device support member 80. Infusion device support member 80 is shaped to receive, or hold, an infusion device, e.g., an intravenous catheter 95 (FIG. 4). Preferably, infusion device support member 80 includes an infusion device recess 81 that is shaped complementary to infusion device 95, thereby facilitating securing infusion device 95 within infusion device support member 80.

Infusion device support member 80 may also include a support member passageway 83 to further facilitate securing infusion device 95 within infusion device support member 80. In a preferred embodiment, infusion device support member 80 includes support member passageway 83 and infusion device recess 81 that is shaped complementary to the shape of a 14 gauge 1¼" catheter sold by Johnson & Johnson Medical Division of Ethicon, Inc. in Arlington, Tex. under the trademark PROTECIV. Using this embodiment, the right atrium of the heart may be infused with fluid.

Infusion device support member 80 is preferably disposed substantially transverse, or perpendicular, to first clamping member 50 or second clamping member 60. In this embodiment, an operator of infusion clamp 40 may secure infusion clamp 40 to a chambered body, and insert the infusion device through complete passageway 70 and through the wall of the chambered body. It is to be understood, however, that infusion device support member 80, and thus, complete passageway 70, may be disposed along topside surfaces 51, 61, and through clamping members 50, 60, at angles other than substantially perpendicular.

In another embodiment, the present invention is directed to a method of infusing a chambered body with a fluid using infusion clamp 40 discussed above. For example, infusion clamp 40 may include at least two clamping members, 50, 60, complete passageway 70 formed by an aperture disposed through at least one of the at least two clamping members 50, 60, and infusion device support member 80 disposed along one of the at least two clamping members 50, 60 and above complete passageway 70.

In the methods of the present invention, infusion clamp 40 is placed, or moved, into one of the plurality of opened positions and placed on the chambered body. Infusion clamp 40 is then moved from the plurality of opened positions to the closed position, thereby securing infusion clamp 40 to the chambered body. Infusion device, e.g., catheter 95, is then inserted into infusion device support member 80 as discussed above, and inserted through the outer wall of the chambered body to provide fluid access to the cavity of the chambered body. The infusion device is placed in communication with a fluid source thereby permitting fluid to be infused into the cavity of the chambered body from the fluid source. In one specific embodiment, the infusion device is preferably in communication with the fluid source prior to being inserted into infusion device support member 80, through infusion clamp 40, and into the cavity of the chambered body.

Figure 5:
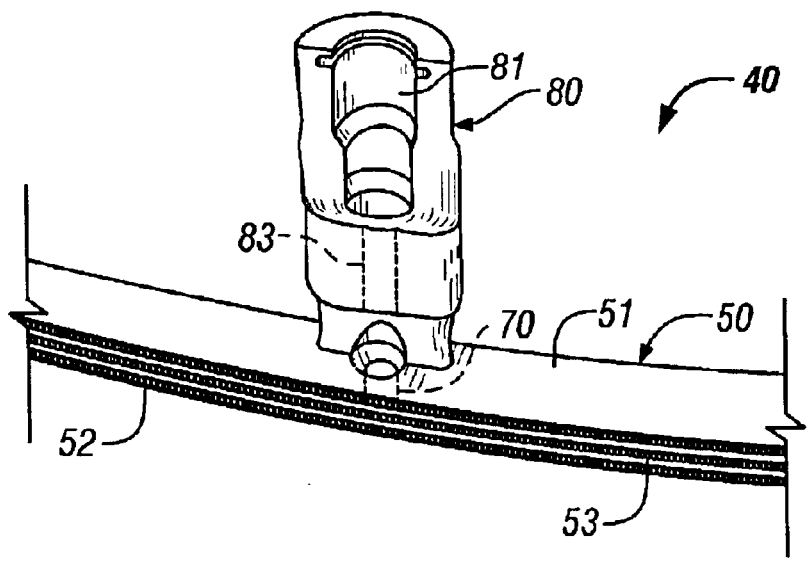
FIG. 5 is a perspective partial view of one clamping member of another embodiment of the infusion clamp of the present invention in one of the plurality of opened positions.
Figure 6:
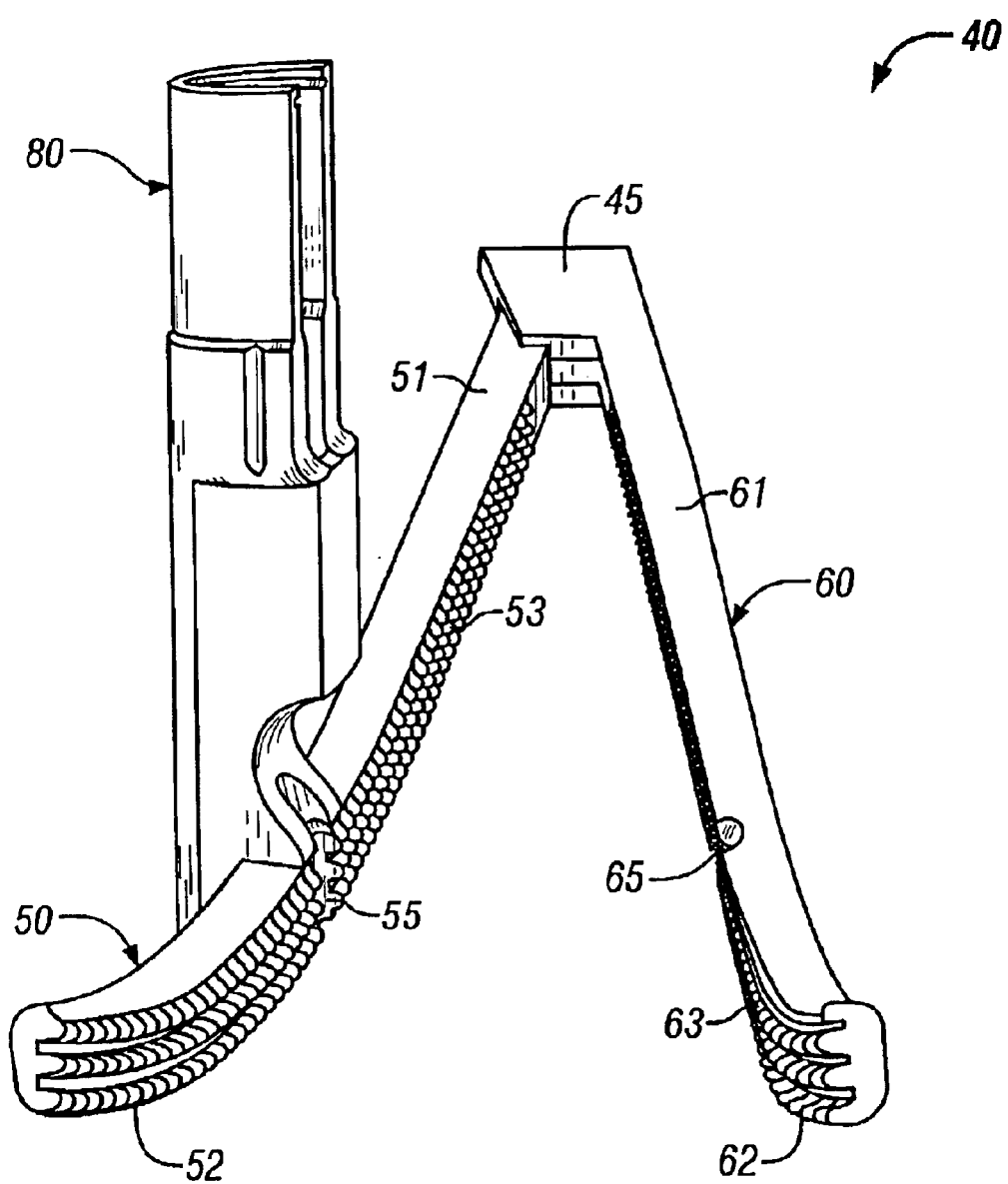
FIG. 6 is a perspective view of another specific embodiment of the infusion clamp of the present invention in one of the plurality of opened positions.

It is to be understood that the invention is not limited to the exact details of construction, operation, exact materials, or embodiments shown and described, as obvious modifications and equivalents will be apparent to one skilled in the art. For example, the infusion device support member may be disposed above a passageway passing through only one of the clamping members (FIG. 5). Additionally, the infusion clamp may include a hinge member disposed at one end with the at least two clamping members extending outwardly from the hinge member, i.e., without the inclusion of gripping members (FIG. 6). Accordingly, the invention is therefore to be limited only by the scope of the appended claims.

What is claimed:

1. An infusion clamp having a plurality of opened positions and a closed position, the infusion clamp comprising:
   a first clamping member having a first side surface, a second side surface, a first mating surface, and an aperture disposed between the first side surface and the second side surface thereby forming a passageway disposed between the first side surface and the second side surface;

a second clamping member having a third side surface, a fourth side surface, and a second mating surface;

a hinge member disposed along and in communication with the first clamping member and the second clamping member, thereby facilitating the movement of the infusion device from the closed position to the plurality of opened positions and from the plurality of opened positions to the closed position; and an infusion device support member disposed above the passageway thereby permitting an infusion device to be disposed within the infusion device support member and through said passageway.

2. The infusion clamp of claim 1, wherein the infusion device support member and the passageway are disposed at an angle substantially perpendicular to the first side surface and the second side surface.

3. The infusion clamp of claim 1, wherein the infusion device support member includes a recess having a shape complementary to the infusion device.

4. The infusion clamp of claim 3, wherein the shape of the recess is complementary to a catheter.

5. The infusion clamp of claim 1, further comprising a gripping member on each clamping member.

6. The infusion clamp of claim 1, further comprising two gripping members and a locking member.

7. The infusion clamp of claim 6, wherein each of the gripping members includes a finger loop.

8. The infusion clamp of claim 1, wherein the first clamping member and the second clamping member are curved shaped.

9. The infusion clamp of claim 1, wherein the first clamping member and the second clamping member each include two ends; and the hinge member is disposed at one of the two ends of each of the first clamping member and the second clamping member.

10. An infusion clamp having a plurality of opened positions and a closed position, the infusion clamp comprising:

a first clamping member having a first side surface, a second side surface, a first mating surface, and a first aperture forming a first partial passageway disposed between the first side surface and the second side surface;

a second clamping member having a third side surface, a fourth side surface, a second mating surface, and a second aperture forming a second partial passageway disposed between the third side surface and the fourth side surface, wherein the first partial passageway and the second partial passageway form a complete passageway when the infusion clamp is placed in the closed position;

a hinge member disposed along and in communication with the first clamping member and the second clamping member, thereby facilitating the movement of the infusion device from the closed position to the plurality of opened positions and from the plurality of opened positions to the closed position; and an infusion device support member disposed above the first partial passageway thereby permitting an infusion device to be disposed within the infusion device support member and through the first partial passageway when the infusion device is placed in one of the plurality of opened positions, and through the complete passageway when the infusion device is placed in the closed position.

11. The infusion clamp of claim 10, wherein the infusion device support member and the complete passageway are disposed at an angle substantially perpendicular to the first side surface and the second side surface.

12. The infusion clamp of claim 10, wherein the infusion device support member includes a recess having a shape complementary to the infusion device.

13. The infusion clamp of claim 12, wherein the shape of the recess is complementary to a catheter.

14. The infusion clamp of claim 10, further comprising a gripping member on each clamping member.

15. The infusion clamp of claim 10, further comprising gripping members and a locking member.

16. The infusion clamp of claim 15, wherein each of the gripping members includes a finger loop.

17. The infusion clamp of claim 10, wherein the first clamping member and the second clamping member are curved shaped.

18. The infusion clamp of claim 10, wherein the first clamping member and the second clamping member each include two ends; and the hinge member is disposed at one of the two ends of each of the first clamping member and the second clamping member.

19. A method of infusing a chambered body having an outer wall and a cavity, the method comprising the steps of:

(a) providing an infusion device;

(b) providing an infusion clamp having a plurality of opened positions, a closed position, at least two clamping members, a hinge member disposed along and in communication with the at least two clamping members, and an infusion device support member, each of the at least two clamping, members including a topside surface, a bottom side surface, a mating surface, and a partial passageway formed between the topside surface and the bottom side surface of the respective clamping members, whereby the partial passageways of each of the clamping members form a complete passageway when the infusion clamp is in the closed position, and the infusion device support member is disposed above the partial passageway of one of the at least two clamping members such that the infusion device is disposed within the infusion device support member and through the partial passageway of one of the at least two clamping members when the infusion clamp is in one of the plurality of opened positions;

(c) placing the infusion clamp on the outer wall of the chambered body and moving the infusion clamp from one of the plurality of opened positions to the closed position thereby securing the infusion clamp the outer wall of the chambered body;

(d) inserting the infusion device into the infusion device support member and through the complete passageway;

(e) inserting the infusion device through the outer wall of the chambered body thereby providing fluid communication with the cavity of the chambered body; and (f) infusing the cavity of the chambered body with at least one fluid through the infusion device.

20. The method of claim 19, wherein the infusion device is connected to a fluid source prior steps (d) and (e).

21. The method of claim 19, wherein step (d) occurs prior to step (c).

22. The method of claim 21, wherein the infusion device is connected to a fluid source prior step (d).

* * * * *